US006454459B1

United States Patent
Sillén et al.

(10) Patent No.: US 6,454,459 B1
(45) Date of Patent: Sep. 24, 2002

(54) DEVICE AND PROCESS FOR THERMAL ANALYSIS OF MOLTEN METALS

(75) Inventors: Rudolf Valentin Sillén, Ronneby; Kjell Pettersson, Karlshamn; Håkan Fransson, Ronneby, all of (SE)

(73) Assignee: Novacast AB, Ronneby (SE)

( * ) Notice: Subject to any disclaimer, the term of this patent is extended or adjusted under 35 U.S.C. 154(b) by 42 days.

(21) Appl. No.: 09/645,303

(22) Filed: Aug. 25, 2000

Related U.S. Application Data

(63) Continuation of application No. PCT/SE99/00163, filed on Feb. 9, 1999.

(30) Foreign Application Priority Data

Feb. 26, 1998 (SE) ................................................ 9800580

(51) Int. Cl.⁷ ............................ G01N 25/02; G01K 1/00
(52) U.S. Cl. ........................ 374/139; 374/26; 164/151.4
(58) Field of Search ...................... 374/26, 139; 164/4.1, 164/151.4, 155.6, 154.6

(56) References Cited

U.S. PATENT DOCUMENTS

| 3,406,736 A | * 10/1968 | Jett et al. ........................ 374/26 |
| 3,818,762 A | 6/1974 | Kraus et al. |
| 3,922,916 A | * 12/1975 | Wickert ........................ 73/354 |
| 4,056,407 A | 11/1977 | Cure |
| 4,116,439 A | * 9/1978 | Chavarria et al. ............ 273/59 |
| 4,274,284 A | * 6/1981 | Hance .......................... 73/354 |
| 4,358,948 A | 11/1982 | Plessers |
| 4,598,754 A | * 7/1986 | Yen et al. ..................... 164/4.1 |
| 4,667,725 A | * 5/1987 | Bäckerub ..................... 164/4.1 |
| 5,447,080 A | * 9/1995 | Falk ......................... 73/864.58 |
| 5,720,553 A | * 2/1998 | Falk ............................. 374/26 |
| 6,102,981 A | * 8/2000 | Lindholm ..................... 75/382 |

FOREIGN PATENT DOCUMENTS

| CH | 626450 | 11/1981 | |
| EP | 95102 A1 | * 11/1983 | ................. 374/139 |
| FR | 2616540 | 12/1988 | |
| JP | 01241353 A | * 9/1989 | ................. 249/174 |
| WO | WO86/01755 | 3/1986 | |
| WO | WO92/06809 | 4/1992 | |
| WO | WO96/23206 | 8/1996 | |

* cited by examiner

Primary Examiner—Diego Gutierrez
Assistant Examiner—Lydia M. DeJesús
(74) Attorney, Agent, or Firm—Burns, Doane, Swecker & Mathis, LLP

(57) ABSTRACT

A device for thermal analysis of molten metals comprising two thermocouples is described. It comprises a mould (1) with a spherical cavity (2), the one thermocouple (3) being placed such that it extends over the central portion of the cavity (2), a cylindrical duct (5) which communicates with the cavity (2) and a cylindrical part (7) which communicates with the lower portion of the cavity (2), the other thermocouple (6) being placed in the transition between the cavity (2) and the cylindrical part (7). A process for thermal analysis of molten metals with the aid of the device is also described. The difference in temperature (11) in the temperature/time curve for the thermocouple which is centrally placed and the lower themocouple which is peripherally placed when the solidus temperature determined by means of the centrally placed thermocouple (3) has been reached is used as a measure of the thermal conductivity.

10 Claims, 1 Drawing Sheet

DEVICE AND PROCESS FOR THERMAL ANALYSIS OF MOLTEN METALS

Figures 1, 2:
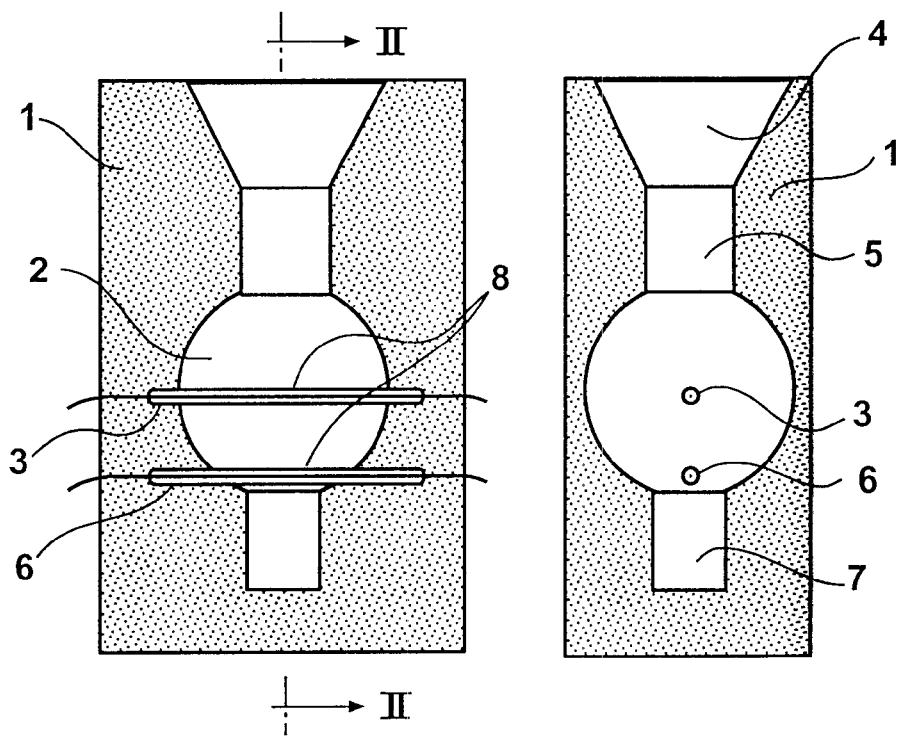

This is a continuation of International Application No. PCT/SE99/00163, filed Feb. 9, 1999, that designates the United States of America and which claims priority from Swedish Application No. 9800580-4, filed Feb. 26, 1998.

The present invention relates generally to thermal analysis of molten metals and in particular to a device and a process for thermal analysis of molten metals.

Industrially used alloys practically always consist of a base metal which has been alloyed with one or more elements. In liquid state, the alloying additives are in most cases soluble in the base metal. The solidification normally takes place within a solidification range which is typical of the alloying composition. Upon solidification, different solid phases are separated from the molten metal, latent heat being released. By following the temperature and the duration in time of the solidification, it is possible to obtain indirectly a reference for the composition of the alloy and its manner of solidification.

The method has been standardised by the use of test cups or crucibles made of refractory material with an integrated expendable thermocouple. The method, which is called thermal analysis, is widely used for iron and aluminium alloys. The cavity in the test cups industrially used is square or circular in cross-section and the test cups are provided with a centrally placed thermocouple. Typical dimensions are 37×37 mm and a height of 40 mm. The cups are made of shell-moulding sand and have a wall thickness of about 5 mm. The cavity is completely open upwards where the metal is poured when testing. From a test, a great deal of information can be obtained about the molten metal and its behaviour, for instance, when casting. The crucial point is to provide a high degree of repeatability of the testing. In prior art, the repeatability can vary, among other things, depending on the filling degree of the test cup and variations in heat emission by radiation and convection from the upper surface.

One problem is that the centrally placed thermocouple only registers temperature conditions in the centre of the cup where the molten metal is liquid for a fairly long time.

It is desirable to be able to simultaneously follow the temperature at the surface of the test cup and carry out a more detailed analysis of the test piece by comparing the process in the centre and surface of the test cup.

Test cups with one thermocouple placed in the centre and another at the surface are already known. Thus Swiss patent specification 626 450 discloses a crucible receiving a molten metal, a thermocouple being arranged in the molten metal and another in or at the wall of the crucible. In other known examples, use has been made of cylindrical or cubic test cups, the thermocouple at the surface being placed at a distance of 1–3 mm from the wall. One problem is that a small error when placing the peripheral thermocouple makes the measuring result uncertain.

The object of the present invention is to solve these problems and provide a device and a process for thermal analysis of molten metals providing high repeatability and high resolution. Hence the device and the process have the features stated in claims 1 and 4, respectively.

In the device according to the invention, the spherical cavity has a cylindrical duct which is connected at the top and a cylindrical part which is connected at the bottom.

Since the cavity is spherical, the solidification will take place in a concentric manner, which makes the impulses from the solidification to the thermocouple placed in the centre much clearer than in known cylindrical or cubic constructions. By arranging a cylindrical filling duct, in which the molten metal has a shorter time of solidification than in the spherical cavity, the effect of fluctuations in the heat emission from the upper surface due to emission changes upon radiation will be eliminated. Furthermore, variations due to different degrees of filling will be eliminated since the duct is assumed to be constantly filled after the casting of a test piece.

By placing the lower thermocouple in the transition between the spherical cavity and the lower cylindrical part, the position can vary somewhat without disturbing the repeatability. The purpose of the lower cylindrical part is that the molten metal located in the same should solidify relatively rapidly and before the molten metal in the spherical cavity. Hence thermal conduction occurs in solid phase through the lower part and during the major part of the solidification in the spherical cavity. Therefore, the lower thermocouple can indirectly register the thermal conductivity of the alloy in semi solid to solid phase.

This is useful in particular when testing cast-iron alloys where carbon is precipitated in the form of graphite with high thermal conductivity during the solidification. The graphite can be precipitated in different forms which affect the castability and physical properties of the alloy. If the graphite is precipitated in the form of spheroids, the alloy is called nodular iron. If the graphite is precipitated in the form of agglomerates with thin graphite flakes, the alloy is called grey cast iron or flake graphite cast iron. The thermal conductivity of flake graphite cast iron can be up to 25% higher than if the graphite has been precipitated in the form of spheroids. An intermediate form is the so-called dense graphite iron, which is distinguished by the graphite being precipitated in the form of rounded "plump" bar-like forms. Thus the thermal conductivity can be used to analyse the graphite form.

According to the present invention, an indirect measure of the thermal conductivity can be obtained by measuring the difference in temperature between the thermocouple placed in the centre and the thermocouple placed peripherally in the spherical cavity in the transition between the spherical cavity and the cylindrical part. According to a preferred embodiment of the invention, the difference in temperature is registered when the solidus temperature of the alloy has been reached at the thermocouple placed in the centre.

Figure 3:
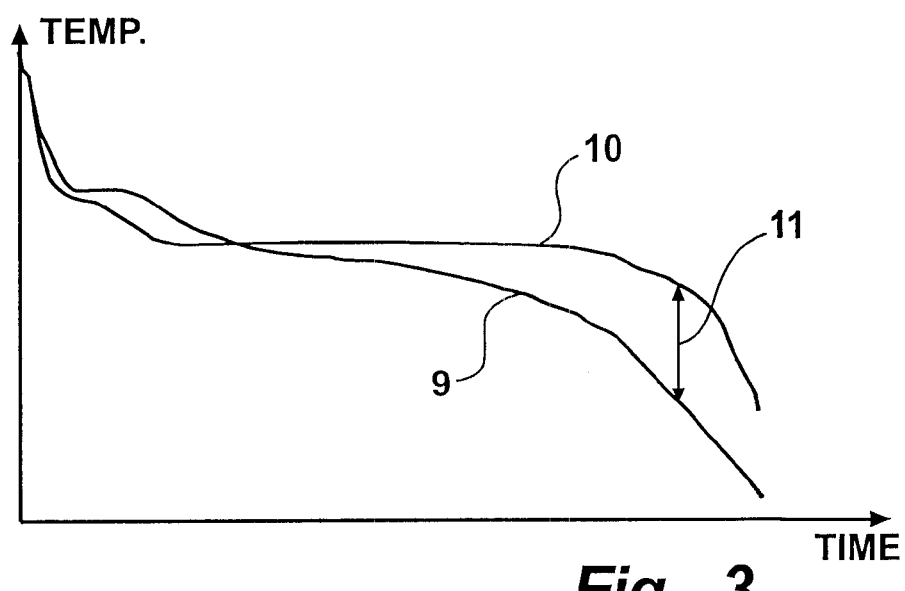

The invention will now be described in more detail with reference to the accompanying drawing, in which FIG. 1 is a front view of a preferred embodiment of the device according to the invention, FIG. 2 is a section along the line II—II in FIG. 1 and FIG. 3 illustrates the temperature curves of the peripheral thermocouple and the central thermocouple.

With reference again to FIGS. 1 and 2, a device is shown comprising a mould 1 consisting of two parts of refractory material. The mould parts are suitably held together during the casting of the test piece by means of a holder (not shown). Furthermore, the device includes a spherical cavity 2 in which a thermocouple 3 is centrally placed. Thus this thermocouple extends over the central portion of the cavity. A pouring cup 4 for pouring molten metal is arranged and this pouring cup passes into a cylindrical duct 5, which in turn communicates with the spherical cavity 2. A cylindrical part 7 is connected to the lower portion of the cavity and a second thermocouple 6 is arranged in the transition between the cavity 2 and the cylindrical part 7. According to this illustrated preferred embodiment, the cold junctions 8 of the thermocouples are positioned along the longitudinal axis of the test cup, the one thermocouple, as mentioned above, extending over the central portion of the spherical cavity 2 and the other thermocouple 6 intersecting the longitudinal axis of the test cup at a short distance above the interface between the cavity 2 and the cylindrical part 7. This distance is generally in the range of 0–2 mm.

The following dimensions can be mentioned as non-limiting examples. The outer dimensions of the mould are a height of 110 mm and a width of 60 mm, the thickness of each mould part being 40 mm. The pouring cup 4 has an upper diameter of 40 mm and a height of 20 mm. The connecting duct 5 has a diameter of 20 mm and a height of 25 mm. The spherical cavity has a diameter of 16 mm and a lower cylindrical part has a diameter of 16 mm and a height of 15 mm. Preferably, the diameter of the duct 5 is 30–50% of the diameter of the spherical cavity 2 and its length is at least 50 % of the diameter of the spherical cavity. Further, in a preferred embodiment, the cylindrical part 7 has a diameter of 30–40% of the diameter of the spherical cavity and its length is greater than 50% of its diameter. The thermocouples 3 and 6 are in prior art manner made of "Chromel-Alumel" and enclosed in a tube of high purity quartz. The thermocouples are connected to an A/D converter in a known manner via a compensating circuit. When analyzing a molten metal, the device is filled with molten metal by means of a casting ladle. The casting temperature for cast-iron alloys should be in the range of 1240–1350°. The temperature is preferably registered once per second. After about 250 s the molten metal is solid. Preferably, time/temperature data are analysed by means of a computer program.

Typical cooling curves are illustrated in FIG. 3. Curve 9 shows the temperature changes of the peripheral thermocouple and curve 10 those of the central thermocouple. The point of time of the solidus temperature of the thermocouple 3 which is placed in the centre is for this purpose defined as the minimum point of the first derivative of the time/temperature curve. The reason why this point of time has been selected is that it is not until after solidification that differences in thermal conductivity become clear. To be able to predict casting properties etc, it is important to obtain a measure of thermal conductivity at the highest possible temperature. At this point of time, the difference 11 in temperature between the thermocouples is calculated. The difference in temperature for molten grey cast iron normally is about 90° C. and for nodular iron alloys which have inferior thermal conductivity about 120° C. The difference in temperature is sufficient not only for classifying the type of cast iron but also for providing information about, for instance, the nodularity of nodular iron alloys and the fraction of vermicular graphite in dense graphite alloys.

What is claimed is:

1. A device for thermal analysis of molten metals comprising:

two thermocouples, a mould with a spherical cavity, one of the thermocouples being placed such that it extends over a central portion of the cavity, a cylindrical duct which communicates with the cavity, and a cylindrical part which communicates with a lower portion of the cavity, the other of the thermocouples being placed in a transition region between the cavity and the cylindrical part.

2. A device according to claim 1, wherein a diameter of the duct is 30–50% of a diameter of the spherical cavity, and a length of the duct is at least 50% of the diameter of the spherical cavity.

3. A device according to claim 1, wherein the cylindrical part has a diameter of 30–40% of a diameter of the spherical cavity, and a length of the cylindrical part is greater than 50% of its diameter.

4. A device according to claim 1, wherein the cylindrical duct is in fluid communication with the cavity, and the cylindrical part is in fluid communication with the lower portion of the cavity such that molten metals may flow from the cylindrical duct to the cylindrical part.

5. A device according to claim 1, wherein a lower end of the cylindrical part defines a closed space.

6. A device according to claim 1, wherein the cylindrical part is disposed beneath the cavity.

7. A device according to claim 1, wherein said one of the thermocouples extending over the central portion of the cavity is disposed horizontally relative to a longitudinal axis of the cylindrical duct.

8. A device according to claim 7, wherein the thermocouple placed in the transition region between the cavity and the cylindrical part is disposed horizontally relative to the longitudinal axis of the cylindrical duct.

9. A process for thermal analysis of molten metals with the aid of the device according to claim 1, said process comprising using, as a measure of the thermal conductivity, the difference in temperature in the temperature/time curve for the thermocouple which is placed centrally and the lower thermocouple which is placed peripherally, when the solidus temperature determined by means of the centrally placed thermocouple has been reached.

10. A process for thermal analysis of molten metals, said process comprising:

providing a device for thermal analysis of molten metals comprising two thermocouples, a mould with a spherical cavity, one of the thermocouples being placed such that it extends over a central portion of the cavity, a cylindrical duct which communicates with the cavity, and a cylindrical part which communicates with a lower portion of the cavity, the other of the thermocouples being placed in a transition region between the cavity and the cylindrical part;

measuring the temperature of the thermocouple which is placed centrally, when the solidus temperature of the molten metals has been reached at the centrally placed thermocouple;

measuring the temperature of the lower thermocouple which is placed peripherally in the spherical cavity in the transition between the spherical cavity and the cylindrical part, when the solidus temperature of the molten metals has been reached at the centrally placed thermocouple;

determining the difference between the temperature of the thermocouple which is placed centrally and the temperature of the lower thermocouple which is placed peripherally in the spherical cavity in the transition between the spherical cavity and the cylindrical part, and thereby indirectly obtaining an indication of the thermal conductivity of the molten metals.

* * * * *